US009053627B2

(12) United States Patent
Yeh

(10) Patent No.: US 9,053,627 B2
(45) Date of Patent: Jun. 9, 2015

(54) INTEGRATED REHABILITATION SYSTEM WITH FEEDBACK MECHANISM

(71) Applicant: PREVENTIVE MEDICAL HEALTH CARE CO., LTD., Taoyuan County (TW)

(72) Inventor: Ching-Yu Yeh, Taichung (TW)

(73) Assignee: PREVENTIVE MEDICAL HEALTH CARE CO., LTD., Taoyuan (TW)

( * ) Notice: Subject to any disclaimer, the term of this patent is extended or adjusted under 35 U.S.C. 154(b) by 271 days.

(21) Appl. No.: 13/902,952

(22) Filed: May 27, 2013

(65) Prior Publication Data

US 2014/0167982 A1 Jun. 19, 2014

(30) Foreign Application Priority Data

Dec. 17, 2012 (TW) ............................ 101147819 A

(51) Int. Cl.

| | |
|---|---|
| ***G08C 19/00*** | (2006.01) |
| ***A61B 5/11*** | (2006.01) |
| ***H04Q 9/00*** | (2006.01) |
| *A63B 24/00* | (2006.01) |

(52) U.S. Cl.

CPC ............. *G08C 19/00* (2013.01); *A61B 5/1127* (2013.01); *A61B 2505/09* (2013.01); *A63B 2024/0012* (2013.01); *H04Q 9/00* (2013.01)

(58) Field of Classification Search

CPC .................. A61B 5/11; A61B 5/1101–5/1128; A61B 2505/09; A63B 24/0006; A63B 2024/0012

See application file for complete search history.

(56) References Cited

U.S. PATENT DOCUMENTS

| | | | | |
|---|---|---|---|---|
| 5,429,140 | A * | 7/1995 | Burdea et al. | 600/587 |
| 5,679,004 | A * | 10/1997 | McGowan et al. | 434/247 |
| 2002/0146672 | A1* | 10/2002 | Burdea et al. | 434/258 |
| 2009/0023122 | A1* | 1/2009 | Lieberman et al. | 434/258 |
| 2009/0264796 | A1* | 10/2009 | Pope et al. | 600/594 |
| 2010/0022351 | A1* | 1/2010 | Lanfermann et al. | 482/1 |
| 2010/0145220 | A1* | 6/2010 | van Vliet | 600/547 |
| 2011/0054870 | A1* | 3/2011 | Dariush et al. | 703/11 |
| 2011/0193699 | A1* | 8/2011 | Van Acht et al. | 340/540 |
| 2013/0060166 | A1* | 3/2013 | Friedman et al. | 600/595 |

* cited by examiner

*Primary Examiner* — Hai Phan
*Assistant Examiner* — Orlando Bousono
(74) *Attorney, Agent, or Firm* — CKC & Partners Co., Ltd.

(57) ABSTRACT

An integrated rehabilitation system with feedback mechanism for a rehabilitant includes a computing center, a memory unit, a plurality of screens, a following module, a plurality of rehabilitation machines, and a feedback module. The memory unit, the screens, the following module, the rehabilitation machines and the feedback module are signally connected with the computing center. A target value of the rehabilitant is stored in the memory unit. A movement-indicating image and a movement mark are displayed on each of the screens. A visual following mark displayed on each of the screens is provided by the following module and corresponds to the target value. Each of the rehabilitation machines corresponds to one of the screens respectively, the movement-indicating image displayed on the screen corresponds to the rehabilitation machine, and the movement mark displayed on the screen corresponds to an operation value generated from the rehabilitation machine.

10 Claims, 6 Drawing Sheets

300 510 300 520 300 530 400 100 610 600 200

INTEGRATED REHABILITATION SYSTEM WITH FEEDBACK MECHANISM

RELATED APPLICATIONS

This application claims priority to Taiwan Application Serial Number 101147819, filed Dec. 17, 2012, which is herein incorporated by reference.

BACKGROUND

1. Field of Invention

The present disclosure relates to a rehabilitation system. More particularly, the present disclosure relates to an integrated rehabilitation system and method thereof.

2. Description of Related Art

A conventional rehabilitation equipment is mostly modified from a fitness equipment which enables repeated exercise of a certain part of a rehabilitant so as to energize the rehabilitant. The conventional rehabilitation equipment has disadvantages as follows. First, when the rehabilitant operates the conventional rehabilitation equipment, a rehabilitation professional is required for providing verbal instructions so as to prevent the rehabilitant from further injury or conducting an ineffective rehabilitation. Second, the monotonously periodic movements of the rehabilitation are boring and frustrating. Third, it is hard for the rehabilitation professional to record a rehabilitation result and to correctively evaluate the progress of the rehabilitant.

In this regard, a rehabilitation system with data feedback mechanism has been developed. The rehabilitation system has a rehabilitation machine and a data feedback mechanism for calculating and saving the data of the rehabilitation machine. A rehabilitant operates the rehabilitation machine and repeats a rehabilitation movement according to the verbal instructions provided by the rehabilitation professional. The rehabilitation machine generates analog signals corresponding to the rehabilitation movement of the rehabilitant. Then the analog signals are sent to a computer and transferred into digital signals at a predetermined time interval, and the digital signals are saved in a database. This kind of rehabilitation system enables the rehabilitation professional to evaluate the progress of the rehabilitant correctly and is favorable for a long-term control and record. Accordingly, the record quality and the evaluation accuracy are improved. However, the rehabilitation system still has some drawbacks.

For example, the rehabilitation process with a single rehabilitation machine is monotonous, and it is hard for the rehabilitant who has been in the abnormal state to correctly follow the verbal instructions of the rehabilitation professional. As a result, the rehabilitation movements of the rehabilitant are frequently inconsistent with the verbal instructions.

Furthermore, the data feedback mechanism for calculating and saving the data is operated under a platform of the single rehabilitation machine, which lacks an integrating function for a complete rehabilitation process. For example, a stroke patient normally experiences three periods during a rehabilitation process: a paralysis period (in which the unilateral body of the stroke patient is week and feeble), a spasm period (in which the muscle tension of the stroke patient increases significantly), and a recovery period (in which the symptoms of paralysis, spasm or paralysis are slight). Each period requires specific rehabilitation machines tailor-made for different kinds of rehabilitation movements, so that the rehabilitation system configured for a single rehabilitation machine cannot satisfy the rehabilitation process of a stroke patient, and the rehabilitation professional cannot gain the complete rehabilitation information via the rehabilitation system.

Given the above, the rehabilitation process provided by the rehabilitation system with data feedback mechanism is monotonous, painful, and ineffective. There is an urgent need to increase the rehabilitation efficiency and to shorten the rehabilitation process in the industry.

SUMMARY

According to an aspect of the present disclosure, an integrated rehabilitation system with feedback mechanism for a rehabilitant includes a computing center, a memory unit, a plurality of screens, a following module, a plurality of rehabilitation machines, and a feedback module. The memory unit is signally connected with the computing center, wherein information of the rehabilitant and a target value of the rehabilitant are stored in the memory unit. The screens are signally connected with the computing center, wherein a movement-indicating image and a movement mark are displayed on each of the screens. The following module is signally connected with the computing center and the memory unit, wherein a visual following mark is provided by the following module to be displayed on each of the screens, and the visual following mark corresponds to the target value of the rehabilitant. The rehabilitation machines are configured for different kinds of rehabilitation movements and signally connected with the computing center, wherein each of the rehabilitation machines corresponds to one of the screens respectively, the movement-indicating image displayed on the screen corresponds to the rehabilitation machine, and the movement mark displayed on the screen corresponds to an operation value generated from the rehabilitation machine. The feedback module is signally connected with the memory unit and the computing center, wherein the feedback module is for integrating and analyzing the operation values provided by the rehabilitation machines.

According to another aspect of the present disclosure, an integrated rehabilitation method applied to a rehabilitation machine with a screen includes steps as follows. A movement-indicating image and a visual following mark are provided and displayed on the screen. A target value is indicated in the movement-indicating image displayed on the screen via the visual following mark. An operation value generated from the rehabilitation machine is provided. A movement mark is provided and displayed on the screen, and the operation value is indicated in the movement-indicating image displayed on the screen via the movement mark. The difference between the movement mark and the visual following mark is monitored and the rehabilitation machine is operated for reducing the difference between the movement mark and the visual following mark.

BRIEF DESCRIPTION OF THE DRAWINGS

The disclosure can be more fully understood by reading the following detailed description of the embodiment, with reference made to the accompanying drawings as follows.

DETAILED DESCRIPTION

Figure 1:
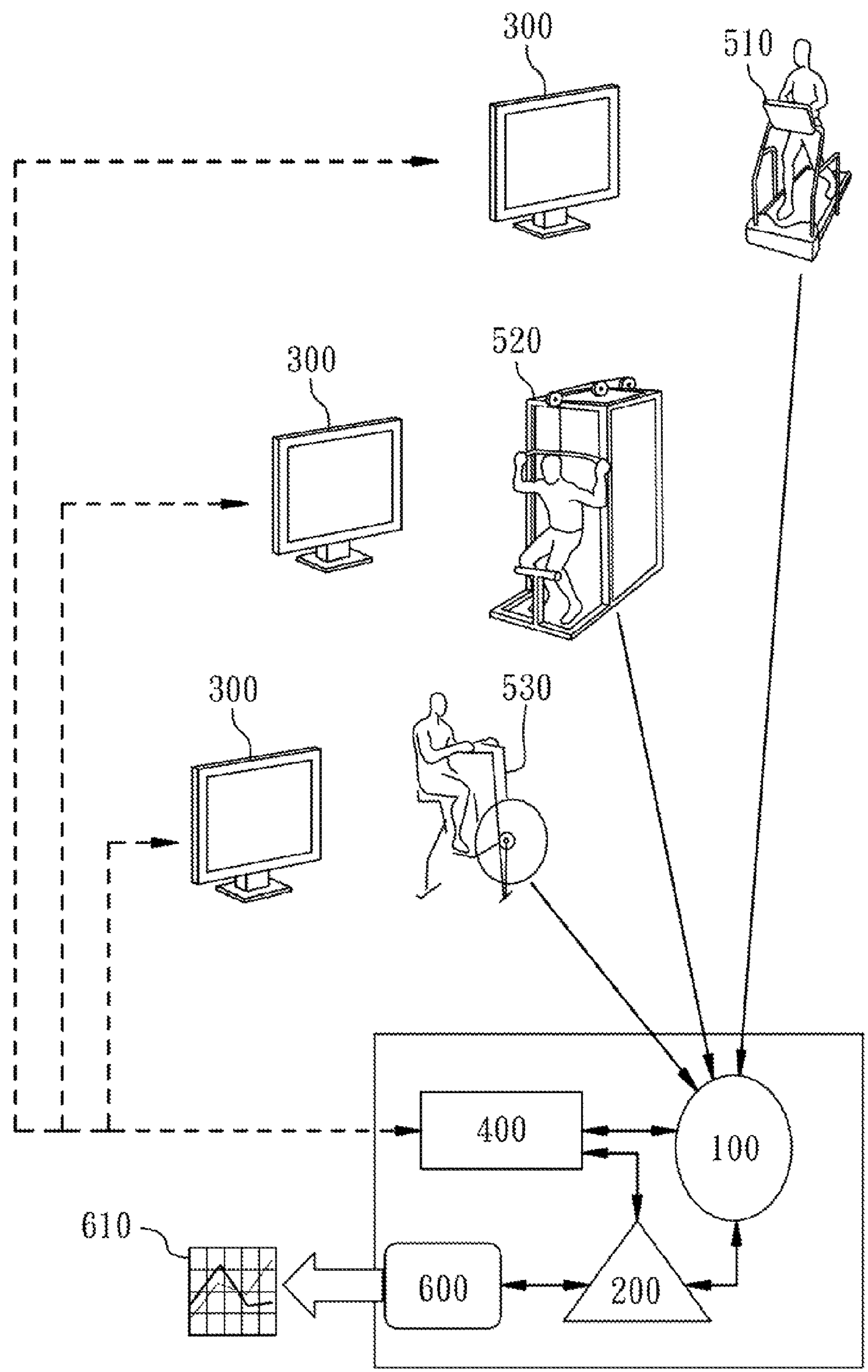
FIG. 1 is a schematic view of an integrated rehabilitation system with feedback mechanism according to one embodiment of the present disclosure.
Figure 2A:
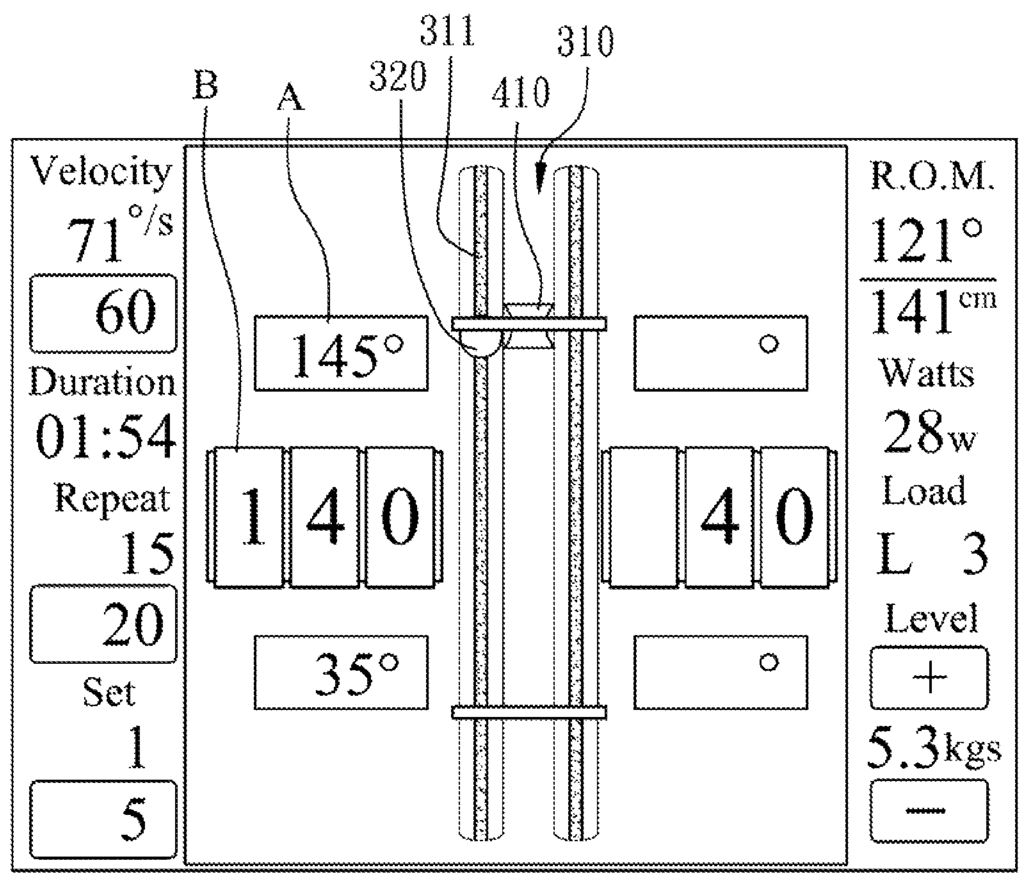
FIG. 2A is a schematic view of a visual following mark and a movement mark in a movement-indicating image according to the embodiment shown in FIG. 1.
Figure 2B:
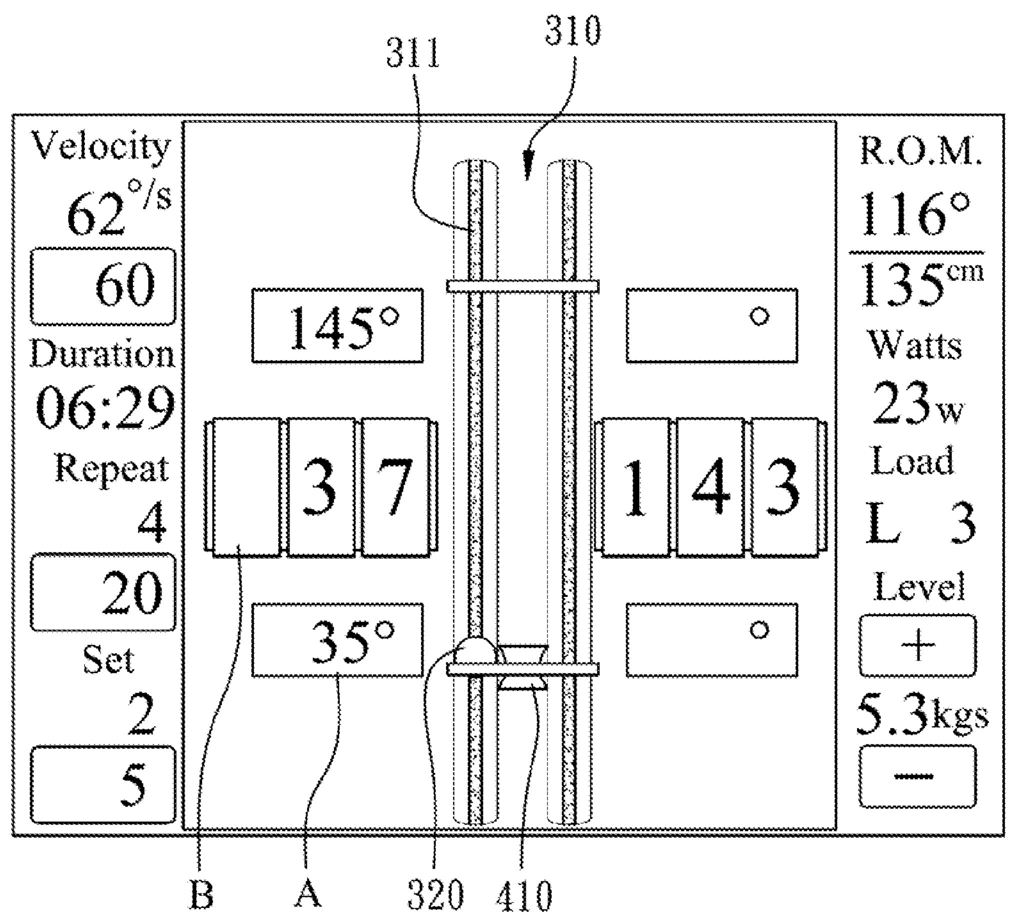
FIG. 2B is a movement schematic view of the visual following mark and the movement mark according to the embodiment shown in FIG. 2A.

FIG. 1 is a schematic view of an integrated rehabilitation system with feedback mechanism according to one embodiment of the present disclosure. FIG. 2A is a schematic view of a visual following mark 410 and a movement mark 320 in a movement-indicating image 310 according to the embodiment shown in FIG. 1. FIG. 2B is a movement schematic view of the visual following mark 410 and the movement mark 320 according to the embodiment shown in FIG. 2A. In FIG. 1, the integrated rehabilitation system with feedback mechanism for a rehabilitant includes a computing center 100, a memory unit 200, three screens 300, a following module 400, a first rehabilitation machine 510, a second rehabilitation machine 520, a third rehabilitation machine 530, and a feedback module 600.

The memory unit 200 is signally connected with the computing center 100. The memory unit 200 is for storing information of the rehabilitant and information inputted by rehabilitation professionals. A target value A of the rehabilitant is also stored in the memory unit 200.

The screens 300 are signally connected with the computing center 100 (via the following module 400), wherein the movement-indicating image 310 and the movement mark 320 are displayed on each of the screen 300. The movement-indicating image 310 shown in FIG. 2A includes a virtual track 311, and the virtual track 311 corresponds to a straight movement path of the first rehabilitation machine 510, the second rehabilitation machine 520 or the third rehabilitation machine 530. The movement mark 320 reciprocates along the virtual track 311.

The following module 400 is signally connected with the computing center 100 and the memory unit 200. A visual following mark 410 is provided by the following module 400 to be displayed on each of the screens 300, and reciprocates along the virtual track 311. The visual following mark 410 reciprocates corresponding to the target value A of the rehabilitant. In other words, the target value A is indicated in the movement-indicating image 310 displayed on the screen 300 via the visual following mark 410.

The first rehabilitation machine 510, the second rehabilitation machine 520 and the third rehabilitation machine 530 are configured for different kinds of rehabilitation movements. The rehabilitation movements are tailor-made for different parts of a human body and are tailor-made for different kinds of muscle exercises of a human body. Each of the rehabilitation machines (i.e., the first rehabilitation machine 510, the second rehabilitation machine 520 and the third rehabilitation machine 530) is signally connected with the computing center 100 and corresponds to one of the three screens 300 respectively. In other words, each of the rehabilitation machines has a corresponding screen 300. Each of the rehabilitation machines corresponds to the movement-indicating image 310 displayed on the corresponding screen 300 and generates an operation value B of the rehabilitant. The movement mark 320 displayed on the corresponding screen 300 reciprocates corresponding to the operation value B of the rehabilitant. In other words, the operation value B is indicated in the movement-indicating image 310 displayed on the screen 300 via the movement mark 320.

The feedback module 600 is signally connected with the memory unit 200 and the computing center 100. The feedback module 600 integrates and analyzes the three operation values B generated from first rehabilitation machine 510, the second rehabilitation machine 520 and the third rehabilitation machine 530, and then output a table 610 showing an integrating and analyzing result.

The aforementioned "signally connected" means that the connection between two objects includes all kinds of signal connections, such as a wired signal connection, a wireless signal connection, a direct signal connection, and an indirect signal connection. For example, the signal connection between the screens 300 and the computing center 100 is an indirect signal connection, as shown in FIG. 1.

In FIG. 2A and FIG. 2B, the movement-indicating mage 310, the visual following mark 410, the movement mark 320, and the virtual track 311 are provided on the screen 300. The target values A and the operation value B are also provided on the screen 300. As described above, the virtual track 311 corresponds to the movement path of one of the three rehabilitation machines, and the visual following mark 410 and the movement mark 320 reciprocate along the virtual track 311 up and down corresponding to the target values A and the operation value B respectively. The target values A can be set in advance as a goal of a rehabilitation plan of the rehabilitant. The operation value B is generated from the rehabilitation machine according a rehabilitation movement of rehabilitant. The target value A can be a speed datum, an angle datum, a frequency datum, a muscle strength datum, a muscular endurance datum or a distance datum, wherein the muscle strength datum and the muscular endurance datum can be obtained via a program calculating the other foregoing data. Similarly, the operation value B can be a speed datum, an angle datum, a frequency datum, a muscle strength datum, a muscular endurance datum or a distance datum, wherein the muscle strength datum and the muscular endurance datum can be obtained via a program calculating the other foregoing data.

When the rehabilitant operates one of the rehabilitation machines and starts the rehabilitation movement, the visual following mark 410 reciprocates corresponding to the target values A, and the movement mark 320 reciprocates corresponding to the operation values B. The rehabilitant can monitor the difference between the movement mark 320 and the visual following mark 410, and operate the rehabilitation machine for reducing the difference between the movement mark 320 and the visual following mark 410, so that the rehabilitant can reach the goal of the rehabilitation plan. Accordingly, the rehabilitant can complete the rehabilitation plan without the verbal instructions provided by the rehabilitation professionals, and the rehabilitation professionals can obtain the conditions of the rehabilitant precisely.

Figure 3A:
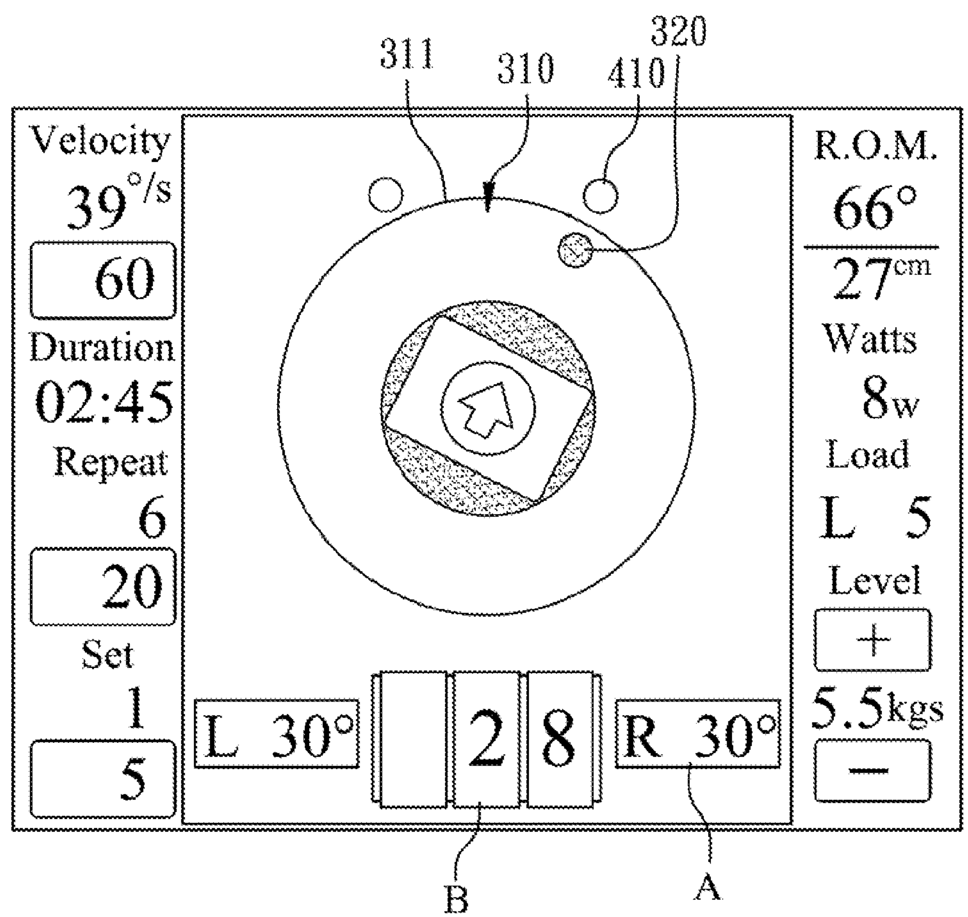
FIG. 3A is another schematic view of a visual following mark and a movement mark in a movement-indicating image according to the embodiment shown in FIG. 1.
Figure 3B:
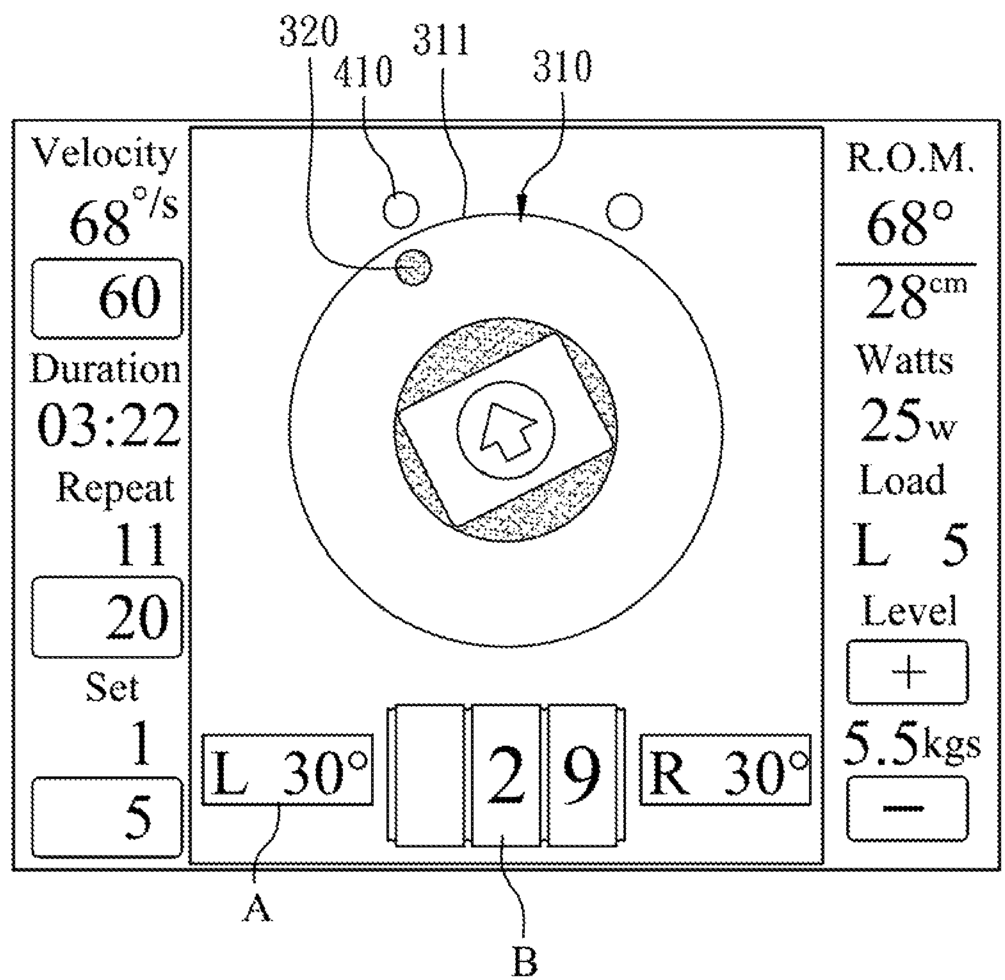
FIG. 3B is a movement schematic view of the visual following mark and the movement mark according to the embodiment shown in FIG. 3A.

FIG. 3A is another schematic view of the visual following mark 410 and the movement mark 320 in the movement-indicating image 310 according to the embodiment shown in FIG. 1. FIG. 3B is a movement schematic view of the visual following mark 410 and the movement mark 320 according to the embodiment shown in FIG. 3A. As mentioned above, each of the first rehabilitation machine 510, the second rehabilitation machine 520 and the third rehabilitation machine 530 has the corresponding movement-indicating image 310. The movement-indicating image 310 shown in FIG. 3A and FIG. 3B corresponds to another rehabilitation machine other than the one corresponding to the movement-indicating image 310 shown in FIG. 2A and FIG. 2B. (If the movement-indicating image 310 shown in FIG. 2A and FIG. 2B corresponds to the first rehabilitation machine 510, the movement-indicating image 310 shown in FIG. 3A and FIG. 3B corresponds to the second rehabilitation machine 520 or the third rehabilitation machine 530.) In FIG. 3A and FIG. 3B, the virtual track 311 corresponding to the movement path of the rehabilitation machine is circular, and the visual following mark 410 and the movement mark 320 reciprocate along the virtual track 311 corresponding to the target values A and the operation value B respectively. Therefore, the rehabilitant can adjust the rehabilitation movement for reducing the difference between the visual following mark 410 and the movement mark 320 so as to reach the goal of the rehabilitation plan.

Furthermore, the feedback module 600 integrates and analyzes the three operation values B generated from first rehabilitation machine 510, the second rehabilitation machine 520 and the third rehabilitation machine 530, and then outputs a table 610 showing the integrating and analyzing, result, so that the rehabilitation professionals can evaluate the result of the rehabilitation plan.

Figure 4:
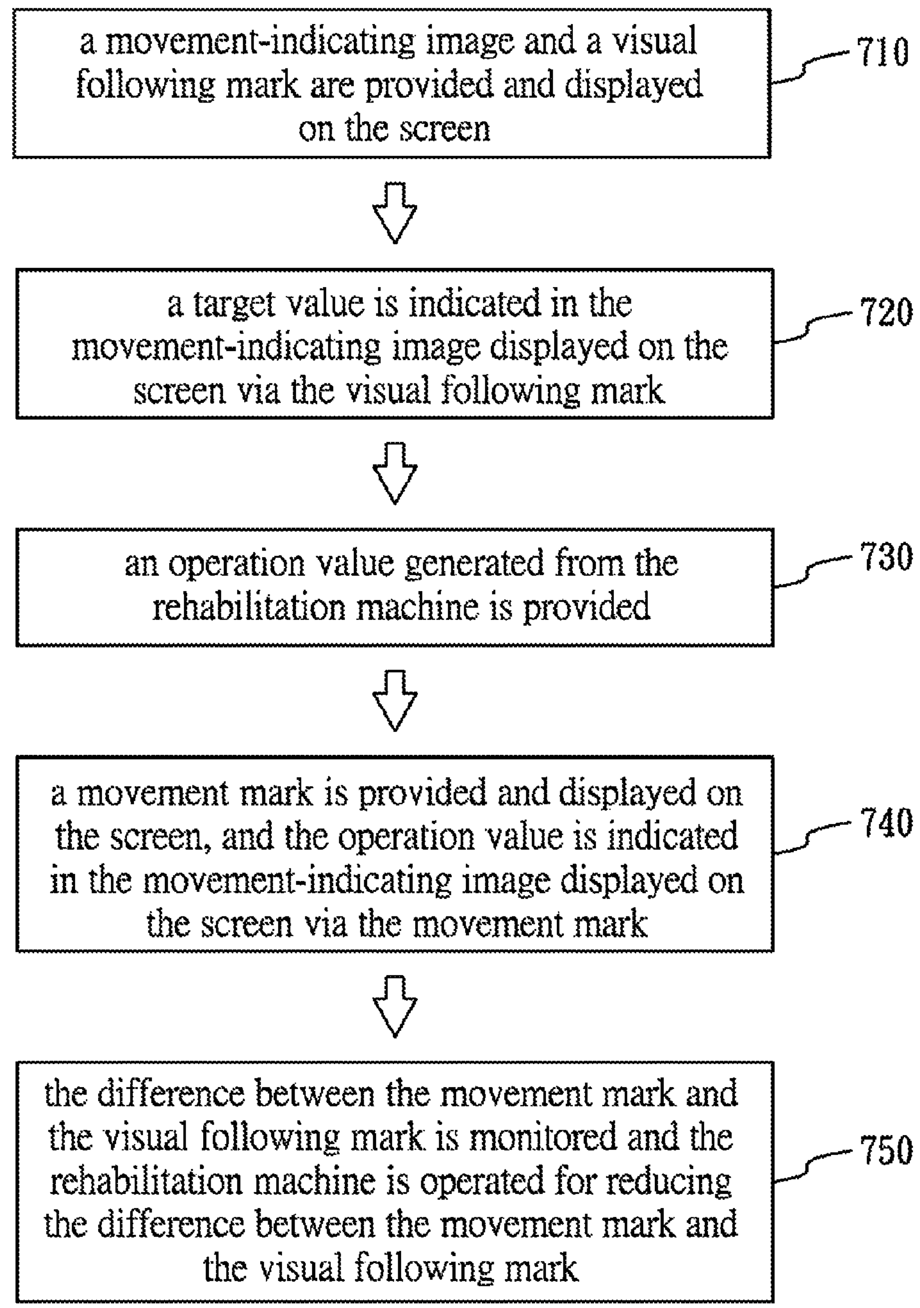
FIG. 4 is a step flow diagram of an integrated rehabilitation method according to another embodiment of the present disclosure.

FIG. 4 is a step flow diagram of an integrated rehabilitation method according to another embodiment of the present disclosure. The integrated rehabilitation method applied to a rehabilitation machine with a screen includes steps as follows.

In Step 710, a movement-indicating image and a visual following mark are provided and displayed on the screen.

In Step 720, a target value is indicated in the movement-indicating image displayed on the screen via the visual following mark.

In Step 730, an operation value generated from the rehabilitation machine is provided.

In Step 740, a movement mark is provided and displayed on the screen, and the operation value is indicated in the movement-indicating image displayed on the screen via the movement mark.

In Step 750, the difference between the movement mark and the visual following mark is monitored and the rehabilitation machine is operated for reducing the difference between the movement mark and the visual following mark.

A software program such as C language (for example, object sequence diagram (OSD)) or Keil C language can be utilized in the integrated rehabilitation method. Furthermore, a chip such as a memory integrated circuit chip, a logic integrated circuit chip, a micro component integrated circuit chip, an analog integrated circuit chip can be utilized in the integrated rehabilitation method. A read-only memory (ROM) can also be utilized in the integrated rehabilitation method.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. An integrated rehabilitation system with feedback mechanism for a rehabilitant, the integrated rehabilitation system comprising:

a computing center;

a memory unit signally connected with the computing center, wherein information of the rehabilitant and a target value of the rehabilitant are stored in the memory unit;

a plurality of screens signally connected with the computing center, wherein a movement-indicating image and a movement mark are displayed on each of the screens;

a following module signally connected with the computing center and the memory unit, wherein a visual following mark is provided by the following module to be displayed on each of the screens, and the visual following mark corresponds to the target value of the rehabilitant;

a plurality of rehabilitation machines configured for different kinds of rehabilitation movements and signally connected with the computing center, wherein each of the rehabilitation machines corresponds to one of the screens, respectively, the movement-indicating image displayed on each of the screens corresponds to a respective rehabilitation machine, and the movement mark displayed on each of the screens corresponds to an operation value generated from each of the rehabilitation machines; and a feedback module signally connected with the memory unit and the computing center, wherein the feedback module is for integrating and analyzing the operation values provided by the plurality of rehabilitation machines, wherein a difference between the movement mark and the visual following mark is monitored and each of the rehabilitation machines is operated for reducing the difference between the movement mark and the visual following mark.

2. The integrated rehabilitation system with feedback mechanism of claim 1, wherein the target value of the rehabilitant is a speed datum, an angle datum, a frequency datum, a muscle strength datum, a muscular endurance datum or a distance datum.

3. The integrated rehabilitation system with feedback mechanism of claim 1, wherein the operation value is a speed datum, an angle datum, a frequency datum, a muscle strength datum, a muscular endurance datum or a distance datum.

4. The integrated rehabilitation system with feedback mechanism of claim 1, wherein the rehabilitation movements are tailor-made for different parts of a human body.

5. The integrated rehabilitation system with feedback mechanism of claim 1, wherein the rehabilitation movements are tailor-made for different kinds of muscle exercises of a human body.

6. An integrated rehabilitation method applied to a plurality of rehabilitation machines with a plurality of screens, the integrated rehabilitation method comprising:

storing information of a rehabilitant and a target value of the rehabilitant in a memory unit;

providing a movement-indicating image and a movement mark displayed on each of the screens;

providing a visual following mark displayed on each of the screens, the visual following mark corresponding to the target value of the rehabilitant;

configuring the plurality of rehabilitation machines for different kinds of rehabilitation movements, each of the rehabilitation machines corresponding to one of the screens, respectively;

providing an operation value generated from each of the rehabilitation machines, wherein the movement mark displayed on a corresponding screen of each of the rehabilitation machines indicates the operation value in the movement-indicating image displayed on the corresponding screen via the movement mark;

integrating and analyzing the operation values provided by each of the rehabilitation machines; and monitoring a difference between the movement mark and the visual following mark and operating each of the rehabilitation machines for reducing the difference between the movement mark and the visual following mark.

7. The integrated rehabilitation method of claim 6, wherein the target value and the operation value are sent to a feedback module for being integrated and analyzed.

8. The integrated rehabilitation method of claim 6, wherein the movement-indicating image comprises a virtual track, and the visual following mark and the movement mark reciprocate along the virtual track.

9. The integrated rehabilitation method of claim 6, wherein the target value of the rehabilitant is a speed datum, an angle datum, a frequency datum, a muscle strength datum, a muscular endurance datum or a distance datum.

10. The integrated rehabilitation method of claim 6, wherein the operation value is a speed datum, an angle datum, a frequency datum, a muscle strength datum, a muscular endurance datum or a distance datum.

* * * * *